US011202359B2

(12) United States Patent
Seipel

(10) Patent No.: US 11,202,359 B2
(45) Date of Patent: Dec. 14, 2021

(54) PROTECTION MEANS AGAINST ELECTROMAGNETIC WAVES AND FIELDS

(71) Applicant: VIVOBASE GmbH, Pliezhausen (DE)

(72) Inventor: Jochen Seipel, Pliezhausen (DE)

(73) Assignee: Vivobase GmbH, Pliezhausen (DE)

( * ) Notice: Subject to any disclaimer, the term of this patent is extended or adjusted under 35 U.S.C. 154(b) by 0 days.

(21) Appl. No.: 16/901,039

(22) Filed: Jun. 15, 2020

(65) Prior Publication Data

US 2020/0396816 A1 Dec. 17, 2020

(30) Foreign Application Priority Data

Jun. 14, 2019 (DE) .......................... 102019116324.2
Dec. 23, 2019 (DE) .......................... 102019135778.0

(51) Int. Cl.
H05F 3/06 (2006.01)

(52) U.S. Cl.
CPC ...................... H05F 3/06 (2013.01)

(58) Field of Classification Search
CPC ... H05F 3/06; A61N 1/16; H05K 9/00; H05K 9/0071
USPC ........................................................ 361/231
See application file for complete search history.

(56) References Cited

U.S. PATENT DOCUMENTS

| 6,611,412 | B1 * | 8/2003 | Reichwein | ............... | A61N 1/16 250/515.1 |
| 6,888,486 | B2 | 3/2005 | Koenig | | |
| 11,063,589 | B1 * | 7/2021 | Mweene | ............... | H03K 17/687 |
| 2002/0189869 | A1 * | 12/2002 | Yeh | .......... | G06F 3/046 178/18.01 |
| 2008/0297676 | A1 * | 12/2008 | Kimura | ................. | H01L 27/124 349/39 |
| 2012/0235587 | A1 * | 9/2012 | Binh | .................... | H03K 5/1534 315/201 |
| 2014/0268941 | A1 * | 9/2014 | Stepps | ................ | H02M 1/4266 363/53 |
| 2016/0158541 | A1 | 6/2016 | Koenig | | |

FOREIGN PATENT DOCUMENTS

| DE | 102014004280 A1 | 10/2015 |
| DE | 10217001327 A1 | 8/2018 |
| DE | 102017001327 A1 | 8/2018 |
| DE | 102107001327 A1 | 8/2018 |
| DE | 10201701926 A1 | 5/2019 |

(Continued)

OTHER PUBLICATIONS

German Search Report in DE 102019135778.0, dated May 20, 2020.

(Continued)

Primary Examiner — Dharti H Patel
(74) Attorney, Agent, or Firm — Irving M. Fishman

(57) ABSTRACT

Device for protection against electric and/or magnetic fields, in particular electromagnetic fields, comprising a switch and a field coupled with the switch, wherein the switch has at least two protection elements, wherein a protection element comprises at least one film capacitor and at least one diode. The switch emits nature-like wave packets, generated by the diodes and capacitors by spontaneous discharges into the environment and the electric field of the power line, whereby the signals correspond to the electric discharges of AIS. A method for operating such a device is also provided.

20 Claims, 3 Drawing Sheets

(56) References Cited

FOREIGN PATENT DOCUMENTS

DE  102017010926 A1  5/2019
RU      94028406 A1  8/1996

OTHER PUBLICATIONS

Eurasian Patent Office Search Reposrt dated Jan. 26, 2021 in EU application Ser. No. 202091216/26 corresponding to the instant application (4 pages).
European Search Report dated Nov. 12, 2020 in EPO Ser. No 20179748.7 corresponding to the instant application (6 pages).
German Search Report dated Dec. 22, 2020 in corresponding German application to the instant application (6 pages).

* cited by examiner

PROTECTION MEANS AGAINST ELECTROMAGNETIC WAVES AND FIELDS

The invention relates to a device for protection against electric and/or magnetic fields, in particular electromagnetic fields, and a method for operating such a device.

BACKGROUND OF THE INVENTION

Loads for living beings generated by electromagnetic waves and fields can occur through: power cables, induction hobs, electric motors, inverters, radio waves and TVs, radio controlled watches and mobile phone networks such as 3G, 4G, 5G etc. Any unit that wirelessly transmits information will cause electric smog.

Electric smog will disrupt or destroy naturally occurring charges in nature. Humans also generate fields and have adapted to nature. These fields are essential for them. Magnetic crystals present in the human brain enable humans to perceive the slightest charges or fluctuations. These fluctuations are perceived subconsciously as stress or loads.

The technical fields that trigger electrosmog have an extremely constant periodicity and a high order compared to natural fields, whereas natural fields have a certain aperiodicity and disorder. Living beings also have a certain ratio of ordered and disordered fields in their electromagnetic composition. Through exposure to electrosmog, humans experience an excess of ordered fields. Sensitive persons can react to this with stress and disorientation. A remedy can be the supply of nature-like wave packets, which can balance out the disproportion between order and disorder.

SUMMARY OF THE INVENTION

It is the task of the present invention to provide a protection means against electromagnetic waves and fields, so that the disrupted balance of naturally occurring charge fields and the fields of the human and those of other life forms or, the relationship between order and disorder through the creation of nature-like fields, is reinstated in a simple way.

The solution according to the invention is realised with the characteristics of the independent claims. Advantageous further developments of the invention result from the subclaims.

The following knowledge underlies the invention. As shown in FIG. 1 switch 1 consists of two so-called vivobase elements 4. A vivobase element 4 consists of a polypropylene film capacitor 5 and a blocking diode 8. The capacitor 5 is connected to the network on one side only. The diode 8 is fitted parallel to the capacitor 5, the blocking layer faces the network connection. One element is then connected with the voltage-carrying conductor and one element with the neutral conductor. The capacitor 5 has a capacity of 0.022 μF and is loadable up to 1,000 V DC.

The unipolar connection of vivobase element 4 creates a potential gradient across the capacitor to its surroundings, which leads to its charging. If the charge of the capacitor 5 exceeds the reverse voltage of the blocking diode 8, a spontaneous discharge of the capacitor occurs, which, similar to a thunderstorm discharge, creates a wave packet in the range of 100 Hz to 18 kHz. By arranging the diodes 8 in opposite directions in the vivobase elements 4, both half-waves of the driving alternating voltage can be utilized.

The solution of the task according to the invention is realised by a device for protection against electric and/or magnetic fields, in particular electromagnetic fields, comprising a switch and a field coupled with the switch. The switch has at least two protection elements. A protection element comprises at least one film capacitor and at least one diode. The circuit uses spontaneous discharges to create wave packets similar to natural, atmospheric impulse radiation (AIS). The switch transmits the interference of the diodes, as well as the frequency generated from the resonance characteristics of the capacitor and the diode, into the electric field. The combination of the signals equals the electrical discharges as with sferics.

The measures according to the invention create a device that is characterised by a protection means against electromagnetic fields, wherein these are nature-like electromagnetic waves/fields and electrostatic waves/fields (electric smog), for all living beings at all times and in all places. The effect of the device, hereafter also called vivobase, reinstates the disrupted balance of naturally occurring charge fields and the fields of humans and other living beings. The vivobase appropriates the effect of nature.

The unipolar connection of the protective elements creates a potential gradient with respect to the environment, which charges the capacitor as the amplitude of the control voltage increases. If the charge reaches the threshold voltage of the diode, the capacitor is short-circuited and a spontaneous discharge occurs. This process is repeated at the next half-wave of the mains frequency/excitation frequency with the same polarity. An opposite arrangement of the diodes allows the use of both half-waves of the mains frequency/excitation frequency. The spontaneous discharges generate wave packets similar to natural, atmospheric impulse radiation (AIS).

An electric field is created between the protection elements. A signal is emitted in this field by the switch, which is called base switch, which consists of the base interference of the diode and the resonance frequency of capacitor and diode, generated in that the capacitor is charged as the amplitude increases and is short-circuited when the threshold voltage of the diode is reached. This process is repeated until the amplitude of the network frequency/excitation frequency falls below the threshold voltage once more. This signal combination equals the electrical discharges, as with sferics.

Sferics, or atmospheric impulse radiation (AIS), is produced by electrical discharges of the atmosphere at high altitude around the entire globe and is therefore invisible to the eye. They cause the pulsed appearance of electromagnetic waves of natural origin within the earth's atmosphere Sferics are created through electrical discharges, like those for example found in a cloud. Unlike lightening during a thunderstorm, sferics are invisible to the eye. Sferics occurrences can be recognised with measuring equipment one or two hours prior to the approach of a thunderstorm.

Sferics (abbreviation of the English atmospherics; sometimes also atmospheric impulse radiation or AIS) are understood as the pulsed occurrence of electromagnetic waves of a natural origin within the earth's atmosphere. Sferics are very brief wave packets, often consisting of just a few vibrations, which are generated by charge displacements. They are so-called dampened vibrations. Their frequencies lie between 3 and 100 kHz.

Sferics or AIS occurrences can also be observed in good weather, but will then have other characteristics than in bad weather, for example during thunderstorms. The differences are for example the height of the amplitudes, the impulse duration and the impulse sequence frequency as well as the frequency of the discharges/displacements.

In other words, the device creates frequency spectrum or interference that copies nature, which maintains the correct rhythm of humans by the supply of nature-like wave pacts.

The generated wave packets also achieve a polarisation of the water molecules in the body of humans and other living beings, so that less electrosmog is absorbed and a positive effect is also achieved in case of thermal stress of electrosmog.

Or to put it another way: The dipolar characteristic of the water molecule and the generated electric field also allow the device to polarise the water molecules present in the human body and protect the human against the thermal load of electric smog in this way.

In one further development the device envisages that the diode is a Shottky diode. It is of advantage here that, firstly: the frequencies of the vivobase units depend on the resonance characteristics of the vivobase elements and their control. It was discovered that Shottky diodes with a shorter refractory period than normal diodes displace the spectrum towards higher frequencies, as these can switch more often i.e. faster at 50 Hz than normal diodes. Secondly: Shottky diodes have a stronger basic interference than normal diodes.

Another further development envisages that the diode of one of the protection elements is connected on the capacitor rotated to the diode of one of the other protection elements. According to one example the diode of one of the protection elements is connected on the capacitor rotated to the diode of one of the other protection elements. One protection element takes on the positive half-wave and another protection element the negative half-wave. The diodes have been connected in the neutral conductor path or on the voltage-carrying capacitor in the same way to date.

In another further development it is envisaged that the film capacitor is an SMD polypropylene film capacitor. According to one example the film capacitor is an SMD polypropylene film capacitor. It has been assumed to date that the desired resonance characteristics, created by the capacity, construction shape, material characteristics and by size, will be realised only with a capacitor like those used until now. The shorter refractory period of the Shottky diodes means that this construction type can also realise the desired resonance characteristics. The switch can thus be constructed in a clearly more space saving way. This offers the possibility of providing protection with the vivobase in any situation.

To improve the device still further it is envisaged in one further development that the switch is operated with different frequencies and/or frequency programs. According to one example the switch is operated with different frequencies. The set frequency and the impulse period resulting from the same controls the intensity of the field. They can therefore influence the perception of a human with regard to the field of the vivobase positively or negatively during the acclimatisation phase.

In another further development it is envisaged that the switch has an amplification switch, which is coupled with at the least two protection elements. According to one example the switch has an amplification switch that is coupled with at least two protection elements. Frequencies and signal forms are therefore routed back to the capacitor diode combination via the amplification switch. This embodiment is also called home variant or corporate variant because it is operated by means of a network voltage of 230 V. The voltage is first commutated and is then re-modulated, so that other frequencies or frequency programs, and also signals forms, can be used.

According to one example the diodes or Shottky diodes are switched parallel to the capacitor. Two diodes are connected with the voltage carrying conductor and two diodes with the neutral conductor.

According to one example the switch has a frequency generator switch, which is coupled with at least two protection elements via a cascade. The frequency switch is driven with a voltage supply, for example a battery or a 12V direct current source. The frequency generator switch is routed to the protection elements comprising the capacitor and the diode via a cascade. With this switch a protection element each is located on the neutral conductor and on the phase. This embodiment is also called mobile variant and is built with such small dimensions that the circuit board can be embedded in a wristband, key ring or a dog tag/collar.

Another further development envisages that the device has a housing with a display. A clock, the condition of the battery or the operating status can be read on the display. Different programs can also be selected, with which the switch can be operated at different frequencies.

According to a further aspect of the invention a method for operating the device is illustrated. The method comprises:

Generation of nature-like wave packets by spontaneous discharge of the capacitors via diodes similar to natural AIS.

A method comprises: control and switching for an interference output of the diodes as well as the frequency generated by the resonance characteristics of the capacitor and the diode, into the electric field; and combining the signals, wherein the combination of the signals equals the electrical discharges as with sferics.

The switch should be operable at different frequencies. The set frequency can positively or negatively influence the perception of a human with regard to the field of the vivobase. The vivobase units will be operable with different frequencies or frequency programs by the switch, as not just one form of AIS or sferics occurs in nature.

Advantageous further developments of the invention result from the subclaims.

BRIEF DESCRIPTION OF THE FIGURES

Further details of the invention can be found in the embodiment examples, which will be described with reference to the Figures. These show.

DETAILED DESCRIPTION OF THE FIGURES

Figure 1:
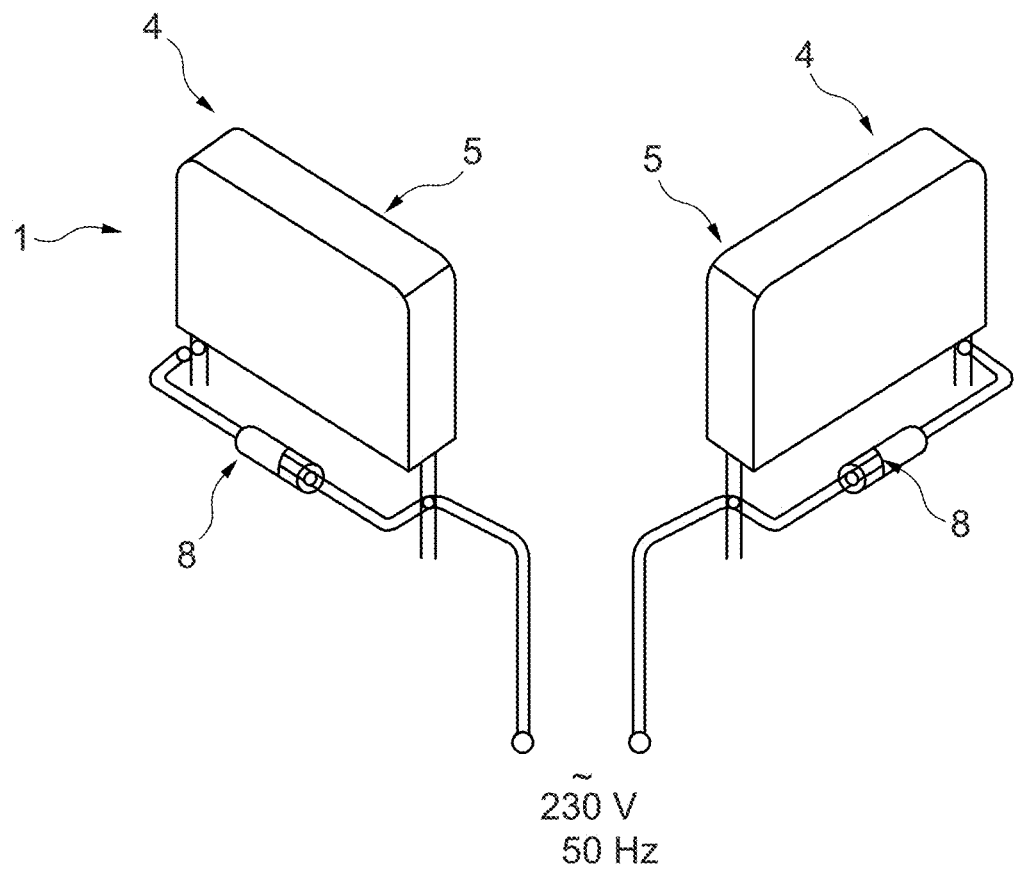
FIG. 1: switch with two vivobase elements.
Figure 2:
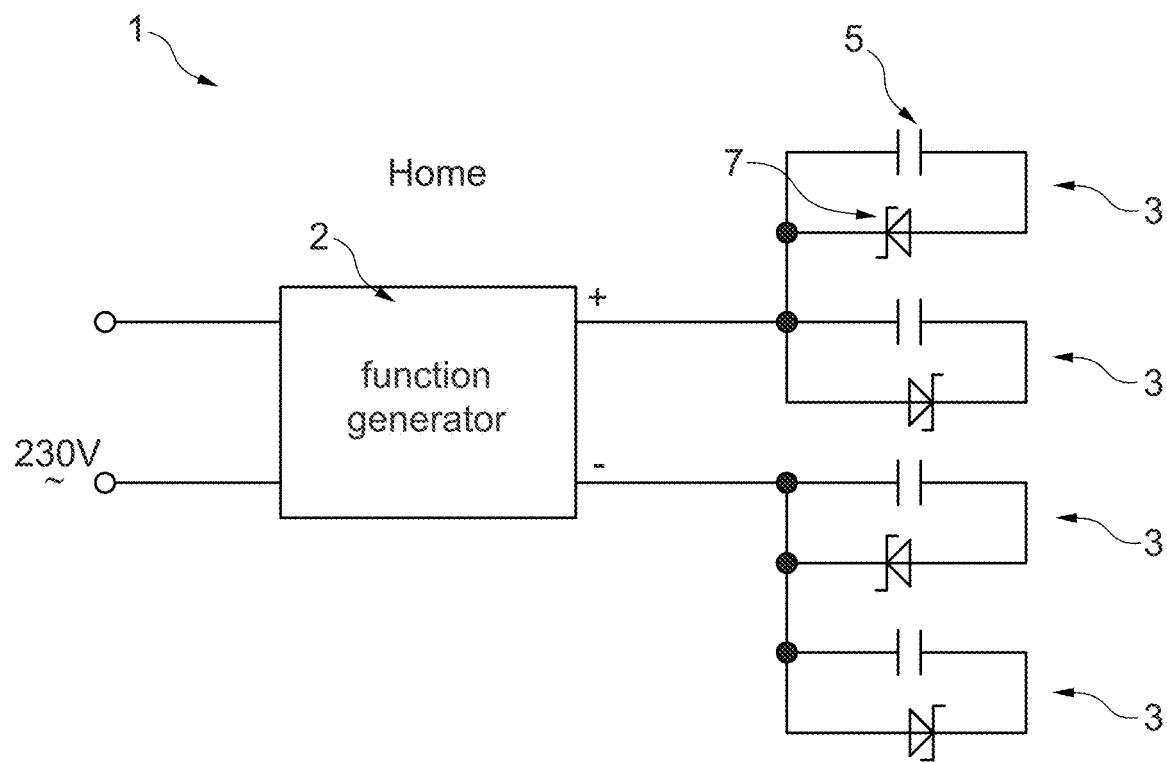
FIG. 2: switch of a device for protection against electric and/or magnetic fields, in particular electromagnetic fields.

Examples of embodiments of the invention will be described hereafter with reference to the enclosed drawings:

FIG. 2 shows a basic switch 1 of a device (vivobase) for protection against electric and/or magnetic fields, in particular electromagnetic fields. This type of basic switch 1 is for example provided for use in a house (home) or in a company (corporate).

The switch 1 has four protection elements 3. Each protection element 3 comprises a film capacitor 5 and a diode 7 in this example (these reference numbers are listed only for one protection element for reasons of clarity).

Switch 1 emits the wave packets of the Vivobase elements protective elements 3 into the environment and the electric field of the power line. The wave packets are similar to the natural AIS.

In other words: The switch 1 transmits the interference of the diodes 7 as well as the frequency generated by the resonance characteristics of the capacitor 5 and the diode 7 into the electric field. The combination of the signals equals the electrical discharges, as with sferics.

The basic switch 1 is operated with 230V mains voltage. The voltage is commutated in the function generator 2 and is then re-modulated, so that other frequencies or frequency programs, and also signal forms, can be used. These frequencies and signal forms are then routed to the capacitor/diode combination 3 via an amplification switch.

Shottky diodes 7 are used parallel to the capacitor 5 in this example; two on the voltage carrying conductor and two on the neutral conductor. A glow lamp with a series resistor can be located between the elements 3.

The operating condition of the device is for example read from a tricolour LED.

Figure 3:
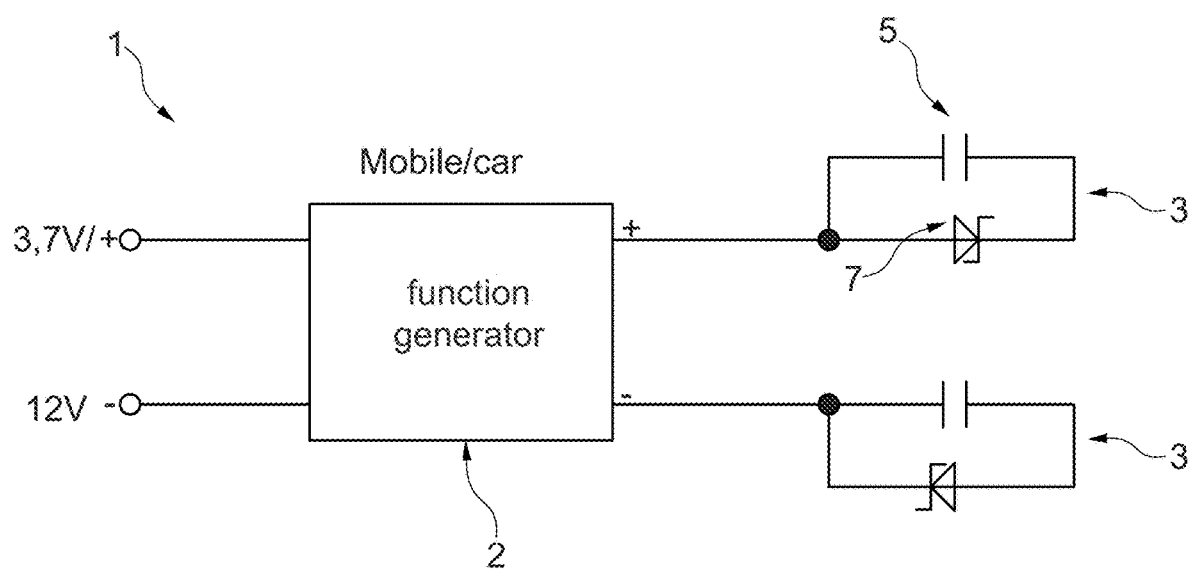
FIG. 3: further switch of a device for protection against electric and/or magnetic fields, in particular electromagnetic fields.

A further basic switch 1 of a device (vivobase) for protection against electric and/or magnetic fields, in particular electromagnetic fields, is shown in FIG. 3. This type of basic switch 1 is for example provided for mobile use (mobile) or in a vehicle (car).

The voltage supplies are a 3.7V battery or a 12V direct current source. This voltage drives a frequency generator switch 2 and is transmitted to the two protection elements 3 via a cascade, each comprising a capacitor 5 and diode 7.

With this switch 1 for a vivobase mobile a capacitor/diode pair 3 each is located on the neutral conductor and on the phase. The same Shottky diodes as those of the example of FIG. 2 (home) are once again used here, wherein the capacitors 5 are replaced with SMD capacitors 5 with the same characteristics.

The voltage supply can be a lithium ion battery, the voltage of which is inverted, amplified, and then transmitted to the two elements 3. The voltage carrying conductor to one element 3 and the neutral conductor to the other element 3. The switch 1 is operated with 25 Hz.

The switch 1 of the vivobase car variant is as for vivobase mobile, except that the voltage supply is a USB interface instead of the battery.

The mobile variant shown in FIG. 3 is constructed so small that one can embed the circuit board in a wristband, key ring or a dog tag/collar.

In some examples these housing variants have a display. A clock, the condition of the battery and the operating status can be read on the display. Different programs can also be selected, with which the switch 1 is operated with different frequencies. The circuit boards in the respective vivobase corporate or vivobase animal variant are the same as those of vivobase home, only the housings differ.

The operating condition of this car variant can also be readable from a tricolour LED. A corresponding program can be permanently set for this.

It should be noted that the methods, devices and systems described in this document can be used on their own as well as in combination with other methods, devices and systems described in this document. All aspects of the methods, devices and systems described in this document can also be combined with each other in multiple ways. The characteristics of the claims in particular can be combined with each other in multiple ways.

The invention has been described in detail with reference to the drawings and the above description. This invention can however be realised in many different forms and should not be interpreted as limited to the embodiments illustrated here; instead these embodiments are provided so that this disclosure is through and complete, and cover the scope of protection of the invention completely for a person skilled in the art. The terminology used in the detailed description of the embodiments illustrated in the enclosed drawings shall not be limiting for the invention. Identical reference numbers in the drawings refer to identical elements.

The invention claimed is:

1. A device for protection against electric and/or magnetic fields, in particular electromagnetic fields, comprising
a switch and
a field coupled with the switch,
wherein the switch has at least two protection elements,
wherein each of said at least two protection elements comprises at least one film capacitor and at least one diode,
characterised in that the at least one diode and the at least one film capacitor generate nature-like wave packets by spontaneous discharge and emits them into the environment and the electric field of the power line, the signals being similar to the electric discharges of AIS.

2. The device, in particular according to claim 1, for protection against electric and/or magnetic fields, in particular electromagnetic fields, comprising
a circuit and
a field coupled to the circuit,
the circuit comprising at least two protection elements
wherein each of said at least two protection elements comprises at least one film capacitor and the at least one diode,
characterised in that the switch transmits the interference of the at least one diode as well as the frequency generated from the resonance characteristics of the at least one film capacitor and the diode, into the electric field, wherein the combination of the signals equals the electrical discharges as with sferics.

3. The device according to claim 2, characterised in that the at least one diode is a Shottky diode.

4. The device according to claim 2, characterised in that the at least one diode of one of the protection elements is connected on the at least one film capacitor rotated to the at least one diode of one of the other protection elements.

5. The device according to claim 2, characterised in that the at least one film capacitor is an SMD polypropylene film capacitor.

6. The device according to claim 2, characterised in that the switch is operated with different frequencies and/or frequency programs.

7. The device according to claim 2, wherein the switch has an amplification switch that is coupled with said at least two protection elements.

8. The device according to claim 7, characterised in that the at least one diode or Shottky diodes are switched parallel to the at least one film capacitor.

9. The device according to claim 2, characterised in that the switch has a frequency generator switch that is coupled with the at least two protection elements via a cascade.

10. The device according claim 2, characterised in that the device has a housing with a display.

11. A method for operating a device according to claim 2, wherein the method comprises:
controlling the switch for emitting nature-like wave packets by means of the at least two diodes and at least two film capacitors into the environment and the electric field of power lines.

12. The device according to claim 1, characterised in that the at least one diode is a Shottky diode.

13. The device according to claim 1, characterised in that the at least one diode of one of the protection elements is connected on the at least one film capacitor rotated to the at least one diode of one of the other protection elements.

14. The device according to claim 1, characterised in that the at least one film capacitor is an SMD polypropylene film capacitor.

15. The device according to claim 1, characterised in that the switch is operated with different frequencies and/or frequency programs.

16. The device according to claim 1, wherein the switch has an amplification switch that is coupled with at least two protection elements.

17. The device according to claim 16, characterised in that the at least one are switched parallel to the at least one film capacitor.

18. The device according to claim 1, characterised in that the switch has a frequency generator switch that is coupled with the at least two protection elements via a cascade.

19. The device according to claim 1, characterised in that the device has a housing with a display.

20. A method for operating a device according to claim 1, wherein the method comprises:
    controlling the switch for emitting nature-like wave packets by means of the diodes and capacitors into the environment and the electric field of power lines.

\* \* \* \* \*

UNITED STATES PATENT AND TRADEMARK OFFICE
CERTIFICATE OF CORRECTION

| | | |
|---|---|---|
| PATENT NO. | : 11,202,359 B2 | |
| APPLICATION NO. | : 16/901039 | |
| DATED | : December 14, 2021 | |
| INVENTOR(S) | : Seipel | |

It is certified that error appears in the above-identified patent and that said Letters Patent is hereby corrected as shown below:

In the Claims

Claim 8, Line 2, delete "or Shottky diodes"

Claim 16, Line 2, after "coupled with" insert --said--

Claim 17, Line 2, after "the at least one" insert --diode--

Claim 20, Line 4, before "diodes" insert --at least two--

Claim 20, Line 4, before "capacitors" insert --the at least two film--

Signed and Sealed this
Tenth Day of May, 2022

Katherine Kelly Vidal
*Director of the United States Patent and Trademark Office*